United States Patent [19]

Yamada et al.

[11] Patent Number: 5,101,062

[45] Date of Patent: Mar. 31, 1992

[54] PROCESS FOR PRODUCING CARBAMIC ACID ESTERS

[75] Inventors: Mutsuo Yamada; Kazumi Murakami; Yasuyuki Nishimura; Fumito Nakajima; Nobuo Matsuo, all of Kure, Japan

[73] Assignee: Babcock-Hitachi Kabushiki Kaisha, Tokyo, Japan

[21] Appl. No.: 405,955

[22] Filed: Sep. 12, 1989

[30] Foreign Application Priority Data

Sep. 13, 1988 [JP] Japan .............................. 63-228947
Oct. 31, 1988 [JP] Japan .............................. 63-275229

[51] Int. Cl.$^5$ ............................................. C07C 269/04
[52] U.S. Cl. ..................................... 560/24; 560/25; 560/28; 560/26; 560/33; 560/157; 560/158; 560/162; 560/163; 560/165; 560/166
[58] Field of Search ................. 560/24, 157, 25, 26, 560/28, 33, 158, 162, 163, 165, 166

[56] References Cited

U.S. PATENT DOCUMENTS

| | | | |
|---|---|---|---|
| 3,993,685 | 11/1976 | Zajacek et al. | 560/24 |
| 4,134,880 | 1/1979 | Miyato et al. | 560/24 |
| 4,178,455 | 12/1979 | Hirai et al. | 560/24 |
| 4,621,149 | 11/1986 | Fukuoka et al. | 560/24 |

FOREIGN PATENT DOCUMENTS

| | | | |
|---|---|---|---|
| 0036895 | 10/1981 | European Pat. Off. | 560/24 |
| 57-45148 | 3/1982 | Japan | 560/24 |
| 57-122055 | 7/1982 | Japan | 560/24 |
| 57-185253 | 11/1982 | Japan | 560/24 |

Primary Examiner—James H. Reamer
Attorney, Agent, or Firm—Fay, Sharpe, Beall, Fagan, Minnich & McKee

[57] ABSTRACT

A process for producing carbamic acid esters (N-phenyl carbamate) which comprises reacting an amino group-containing compound (aniline), oxygen, a nitro group-containing compound (nitrobenzene), a carbon monoxide-containing gas and a hydroxyl group-containing organic compound (ethyl alcohol) in the presence of a compound of a transition metal belonging to Pt group of VIII group (Pd) of the Periodic Table as catalyst, a non-metal halide (HCl) and water.

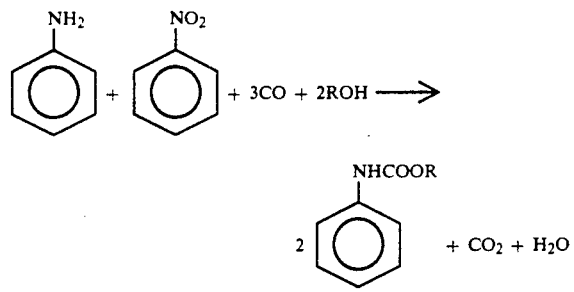

13 Claims, 1 Drawing Sheet

PROCESS FOR PRODUCING CARBAMIC ACID ESTERS

BACKGROUND OF THE INVENTION

1. Field of the Invention

This invention relates to a process for producing carbamic acid esters from an amino group-containing compound, carbon monoxide (CO) and a hydroxyl group-containing compound in the presence of an oxidizing agent.

2. Description of the Related Art

Carbamic acid esters are important as raw materials for pesticides or precursors of isocyanates. Isocyanates have been broadly used as raw materials for urethane products such as soft or hard foams, paints and varnishes, waterproofing agents, adhesives, elastic fibers, etc. Particularly in the case of diphenylmethane diisocyanate (MDI), its new use applications as heat-insulating materials, impact-resistant, light materials for automobiles, etc. has also been extensively developed and its need has been expanded to a large extent.

Carbamic acid esters have been prepared from an isocyanate prepared by the reaction of an amine with phosgene (reaction equation 1) and an alcohol (reaction equation 2) as follows.

$$RNH_2 + COCl_2 \rightarrow RNCO + 2HCl \quad (1)$$

$$RNCO + R'OH \rightarrow RNHCOOR' \quad (2)$$

Phosgene has raised various problems that it is a deadly poison, it uses chlorine requiring a large amount of electric power, conversion process into phosgene is complicated and hydrochloric acid is by-produced in a large amount. Thus, in order to simplify the process and save the energy, a process for producing carbamic acid esters without using phosgene has been researched. For example, in the case of preparation of phenylcarbamic acid esters, mainly three production methods have been researched. The first is a process of preparing a carbamic acid ester from nitrobenzene, CO and an alcohol at one step (reaction equation 3). The second is a process of preparing it from aniline or diphenylurea, nitrobenzene or oxygene, CO and an alcohol (reaction equations 4, 5 and 6). The third is a process of preparing it by first preparing diphenylurea from nitrobenzene, aniline and CO, followed by subjecting the resulting diphenylurea to alcoholysis (reaction equations 7-1 and 7-2).

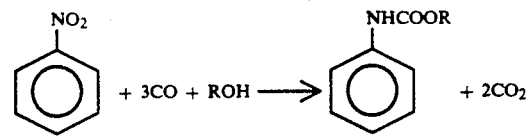

(3)

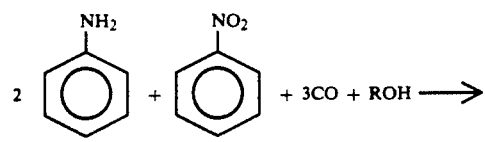

(4)

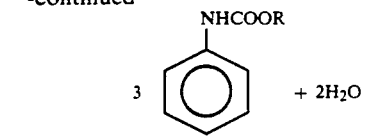

(5)

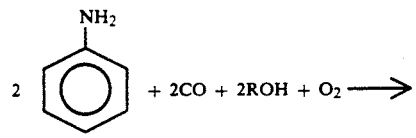

(6)

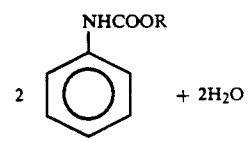

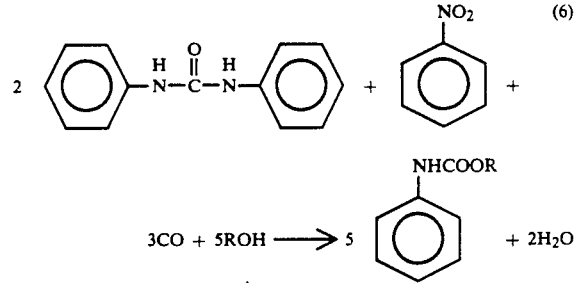

(7-1)

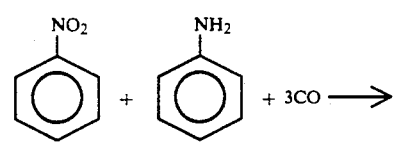

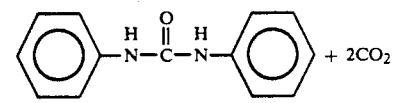

(7-2)

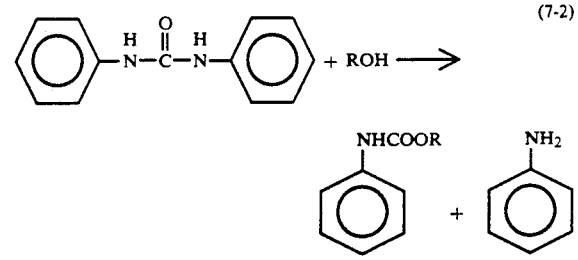

In the reaction equation 3, as the catalyst therefor are used a metal of platinum (Pt) group or its compound and a chloride of compounds of transition metals such as Fe, V, etc. (Japanese patent publication No. Sho 53-33582/ 1978) and/or a tertiary amine such as pyridine (Japanese patent application laid-open No. Sho 51-125216/1976).

In the reaction equations 4 and 6, too, a metal of Pt group or its compound and a compound of transition metals such as Fe are used (Japanese patent application laid-open No. Sho 55-120551/1980). In the reaction equation 5, Pt black and $I^{-1}$ are used (S. Fukuoka et al., Chem. Commun., 1984, 399). Use of transition metal chlorides as promotor raises problems in the aspect of slurrying the reaction solution and separating the product from the catalyst. Further, some catalysts using pyridine requires to make the concentration of expensive Pt group catalyst higher so that a problem of catalyst recovery occurs. On the other hand, in the reaction equations 7-1 and 7-2, no promotor is used, but $Ru_3(CO)_{12}$ cluster catalyst is used (Japanese patent application laid-open No. Sho 62-59252/1987). In this case, slurrying of the reaction solution raises no problem, but there are problems that a long time is required for the reaction and the catalyst activity notably lowers due to a small amount of $H_2$ gas so that $H_2$-containing CO gas cannot be used. In a process where Pd or a Pd compound supported by a carrier and a porous substance are used as a main catalyst and a non-metal halide is used as a promotor in the reaction equation 5 (Japanese patent application laid-open No. Sho 57-122055/1982), slurrying of the reaction solution and separation of the catalyst from the product and catalyst recovery have no problem, but the yield of the product is low.

SUMMARY OF THE INVENTION

The object of the present invention is to provide a process for producing carbamic acid esters under a low pressure and with a high yield and easy handling over the prior art.

The present inventors traced the reaction using aniline, nitrobenzene, ethanol and CO containing 10% of $H_2$ in the presence of 5% Pd/C as catalyst according to the process disclosed in Japanese patent application laid-open No. Sho 57-122055/1982. As a result, almost no carbamic acid ester was formed. Thus, the same experiment as the above except that divalent Pd was used as catalyst was carried out. As a result, a considerable amount of a carbamic acid ester was formed. Thus, the inventors made an extensive research on a process of forming a sufficient amount of carbamic acid esters even when $H_2$-containing CO gas is used. As a result, it has been found that the above-mentioned object can be achieved by adding a small amount of water in advance of the reaction.

The present invention resides in:

a process for producing carbamic acid esters which comprises reacting an amino group-containing compound, at least one of oxygen and a nitro group-containing organic compound, a carbon monoxide-containing gas and a hydroxyl group-containing organic compound in the presence of a compound of a transition metal belonging to Pt group of VIII group of the Periodic Table as catalyst, a non-metal halide and water, the molar ratio of said nitro group-containing organic compound being 0.1 to 2.0 times the molar ratio of the amino group of the amino group-containing compound, the molar ratio of said hydroxyl group-containing organic compound being 3 to 40 times the molar ratio of the amino group of the amino group-containing compound, the pressure of said carbon monoxide-containing gas being in the range of 1 to 50 $Kg/cm^2G$, and molar ratio of said water to be existed in advance of the reaction in terms of the amino group-containing compound being in the range of 0.01 to 2.0

DETAILED DESCRIPTION OF PREFERRED EMBODIMENTS

The drawings are first briefly described.

DRAWINGS

Figure 1:
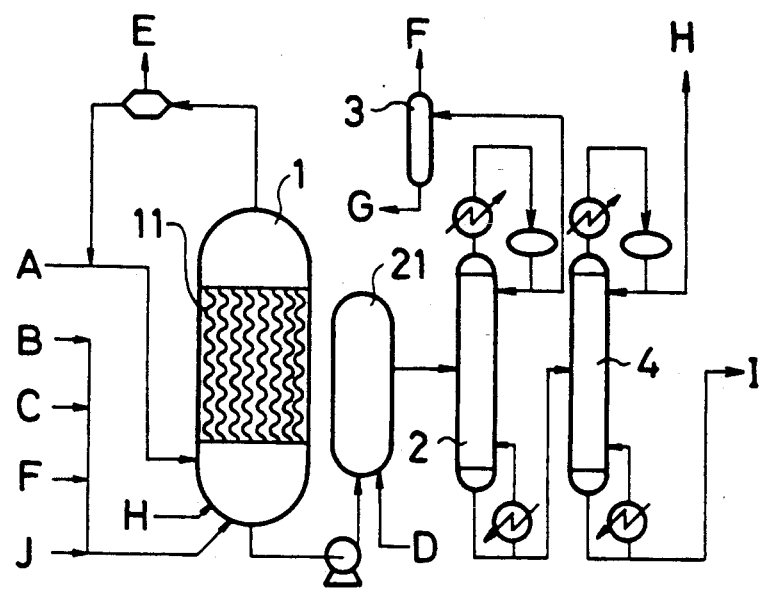
FIG. 1 shows a flowsheet illustrating an embodiment of production of the carbamic acid ester in the present invention.

The reaction equation in the process of the present invention is estimated as follows.

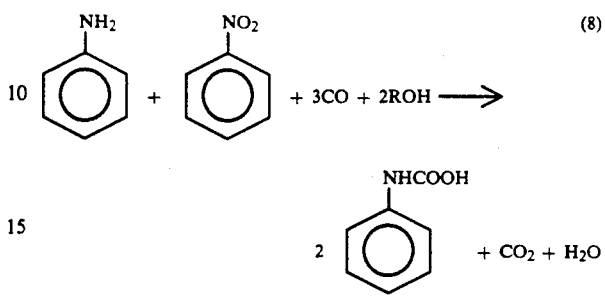

In the case the solution after the reaction contains unreacted raw materials like aniline, nitrobenzene, alcohol, etc. besides the formed carbamic acid ester, there may be a problem that the carbamic acid ester is not easily separated by distillation. In particular, ethyl N-phenylcarbamate as one of carbamic acid esters has a boiling point of 237° C., which is close to that of nitrobenzene i.e. 217° C. In this case, the reaction solution is further contacted with hydrogen-containing gas. As a result, an unreacted nitro group-containing compound is converted into an amino group-containing compound, and separation of carbamic acid ester from the reaction solution by distillation is easily carried out.

When the hydrogen-containing gas is contacted with the resulting reaction solution, aniline is formed from nitrobenzene according to the reaction equation (9) mentioned below and the reaction solution contains no nitrobenzene; hence in the separation by distillation, of ethyl N-phenylcarbamate, it may be sufficient to remove aniline (b.p.: 184° C.) so that the distillation operation may be effected at a lower temperature. As a result, in the distillation of ethyl N-phenylcarbamate, it is possible to improve its purity and yield and reduce the heat quantity required for distillation to a large extent.

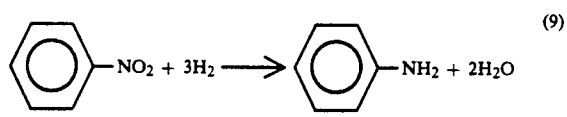

The compound of a transition metal of Pt group used as the catalyst in the present invention is a compound of Pt, Pd, Rh or Ru and these compounds may be used alone or in admixture. Examples of these compounds are halides, thiocyanides, cyanides, isocyanides, nitrates, sulfates, acetates, oxides of these metal. They may be used in the reaction separately from a carrier or may be supported on a carrier. Examples of such a carrier are calcium carbonate, aluminum silicate, magnesium silicate, barium sulfate, titanium oxide, zirconium oxide, silica, alumina, active carbon, graphite, asbestos, bentonite, diatomaceous earth, fuller's earth, organic ion-exchange bodies, inorganic ion-exchange bodies, molecular sieves, etc.

The quantity of the Pt group compound used relative to the amino group-containing compound varies depending on its kind, reaction conditions, etc., but it is preferably used in a range of 1 to $1 \times 10^{-5}$, more preferably $5 \times 10^{-1}$ to $1 \times 10^{-4}$ in a ratio by weight in terms of a metal single substance. Further, the amount of the carrier used is preferably about 5 to 1,000 times, more preferably about 10 to 500 times the weight of the metal single substance.

Examples of the non-metal halides used as the promotor are hydrogen halides such as hydrogen chloride, hydrogen bromide, hydrogen iodide, etc., ammonium halides such as ammonium chloride, ammonium bromide, ammonium iodide, etc., acid halides of sulfur such as thionyl chloride, etc., phosphorus oxyhalides such as phosphoryl trichloride, etc., halogenated benzyl compounds such as benzyl chloride, benzyl bromide, benzyl iodide, etc., halogenated alkyls such as methyl iodide, etc., and among these, hydrogen chloride is particularly preferred. The quantity of the nor-metal halide used as the promotor is about 2 to 1,500 gram atom of halogen, preferably 10 to 700 gram atom per one gram atom of the Pt group metal single substance.

The amino group-containing compound used as a main raw material in the present invention may be any of aromatic monoamines, aromatic polyamines, aliphatic monoamines, aliphatic polyamines, aromatic amino acids or aliphatic amino acids. Examples of the foregoing are aniline, toluidines, xylidines, benzylamines, phenylenediamines, tolylenediamines, aminophenols, naphthylamines, oxynaphthylamines, naphthylenediamines, aminoanthracenes, aminobiphenyls, bis(aminophenyl)alkanes, bis(aminophenyl)ethers, bis(aminophenyl)thioethers, bis(aminophenyl)sulfones, aminodiphenoxyalkanes, heteroaromatic compounds such as aminophenothiazines, 2-aminopyrimidines, aminoisoquinolines, aminoindoles, etc. Concrete compounds thereof are aniline, o-, m- or p-toluidine, 2,3-, 2,4-, 2,5-, 2,6- or 3,4-xylidine, o-, m- or p-phenylenediamine, 2,3-, 2,4-, 2,5-, 2,6- or 3,4-diaminotolylene, benzylamine, xylenediamine, α- or β-naphthylamine, aminobenzoic acid, aminoanthraquinone, o-, m- or p-aminophenol, 1,2-, 1,3-, 1,4-, 1,5-, 1,6-, 1,7-, 1,8-, 2,3-, 2,6- or 2,7-naphthylenediamine, 1-anthramine, o-, m- or p-aminobiphenyl, 1-oxy-2-naphthylamine, 1-oxy-5-naphthylamine, 1-oxy-7-naphthylamine, 1-oxy-8-naphthylamine, 2-oxy-1-naphthylamine, 3-oxy-1-naphthylamine, 4-oxy-1-naphthylamine, 5-oxy-1-naphthylamine, 6-oxy-1-naphthylamine, 7-oxy-1-naphthylamine, 8-oxy-1-naphthylamine, 2,2'-, 2,3'-, 2,4'-, 3,3'-, 3,4- or 4,4'-diaminobiphenyl, 2,2'-, 2,4'-, 3,3'-, 3,4'- or 4,4'-diaminobiphenylmethane, bis(4-aminophenyl)ether, 4,4'-diaminosulfone, bis(4-aminophenoxy)ethane, o-, m- or p-chloroaniline, 4-chloro-1,3-phenylenediamine, p-bromoaniline, 4-fluoro-1,3-phenylenediamine, o-, m- or p-aminophenyleneurethane, o-, m- or p-anisidine, 2,4-diaminophenetol, o-, m- or p-aminobenzaldehyde, p-aminobenzoyl chloride, etc. Further, the isomers, homologues or mixtures of these aromatic amino compounds may also be used.

Examples of the aliphatic amines are primary amines such as methylamine, ethylamine, amylamine, etc., secondary amines such as dimethylamine, diethylamine, etc., alicyclic amines such as cyclopentylamine, cyclohexylamine, etc., diamines such as ethylenediamine, trimethylenediamine, 4,4'-diaminodicyclohexylmethane, hexamethylenediamine, etc., triamines such as 1,2,3-triaminopropane, etc.

Examples of the aliphatic amino acids are monoaminomonocarboxylic acids such as glycine, alanine, etc., oxyamino acids such as serine, threonine, etc., sulfur-containing amino acids such as cysteine, methionine, etc., monoaminodicarboxylic acids such as aspartic acid, glutamic acid, etc., diaminomonocarboxylic acids such as lysine, arginine, etc.; examples of aromatic ring-containing amino acids are phenylalanine, thyrosine, etc.; and examples of heterocyclic ring-containing amino acids are histidine, tryptophan, etc.

The amines or/and amino acids may be used alone or in admixture.

Examples of the hydroxyl group-containing organic compound are monohydric alcohols or polyols which contain primary, secondary or tertiary hydroxyl group, or monohydric or polyhydric phenols. Concrete examples of such alcohols are aliphatic monohydric alcohols such as methyl alcohol, ethyl alcohol, n- or iso-butyl alcohol, n-, iso- or t-butyl alcohol, n- or iso-amyl alcohol, hexyl alcohol, lauryl alcohol, cetyl alcohol, etc., alicyclic monohydric alcohols such as cyclopentanol, cyclohexyl alcohol, etc., aromatic monohydric alcohol such as benzyl alcohol, chlorobenzyl alcohol, methoxybenzyl alcohol, etc., dihydric alcohols such as ethylene glycol, diethylene glycol, propylene glycol, dipropylene glycol, etc., and trihydric alcohols such as glycerol, hexanetriol, etc.

Examples of phenols are monohydric phenols such as phenol, cresol, chlorophenol, ethylphenol, n- or iso-propylphenol, higher alkyl phenols, naphtols, dihydric phenols such as catechol, resorcin, etc. and trihydric phenols such as pyrogallol, fluoroglucinol, etc.

Organic nitro compounds used in the present invention may be any of aromatic mononitro compounds, aromatic polynitro compounds, aliphatic mononitro compounds or aliphatic polynitro compounds. Examples of aromatic nitro compounds are nitrobenzenes, dinitrobenzenes, dinitrotoluenes, nitronaphthalenes, nitroanthracenes, nitrobiphenyls, bis(nitrophenyl)alkanes, bis(nitrophenyl)ethers, bis(nitrophenyl)thioethers, bis(nitrophenyl)sulfones, nitrodiphenoxyalkanes, heteroaromatic compounds such as nitrophenothiazines, 5-nitro-pyrimidine, etc. Examples of concrete compounds are nitrobenzene, o-, m- or p-nitrotoluene, o-nitro-p-xylene, 1-nitronaphthalene, m- or p-dinitrobenzene, 2,4- or 2,6-dinitrotoluene, dinitromesitylene, 4,4'-dinitrobiphenyl, 2,4-dinitrobiphenyl, 4,4'-dinitrodibenzyl, bis(4-nitrophenyl)ether, bis(2,4-dinitrophenyl)ether, bis(4-nitrophenyl)thioether, bis(4-nitrophenyl)thioether, bis(4-nitrophenyl)sulfone, bis(4-nitrophenoxy)ethane, α,α'-dinitro-p-xylene, α,α'-dinitro-m-xylene, 2,4,6-trinitrotoluene, o- m- or p-chloronitrobenzene, 1-chloro-2,4-dinitrobenzene, 1-bromo-4-nitrobenzene, 1-fluoro-2,4-dinitrobenzene, o-, m- or p-nitrophenylcarbamic acid ester, o-, m- or p-nitroanisole, 2,4-dinitrophenetol, m-nitrobenzaldehyde, p-nitrobenzochloride, ethyl p-nitrobenzoate, m-nitrobenzenesulfonyl chloride, p-nitrophthalic anhydride, 3,3'-dimethyl or 4,4'-dinitrobiphenyl, 1,5-dinitronaphthalene, etc. Examples of aliphatic nitro compounds are nitromethane, nitrobutane, 2,2'-dimethylnitrobutane, nitrocyclopentane, 3-methylnitrobutane, nitrooctane, 3-nitropropene-1, phenylnitromethane, p-bromophenylnitromethane, p-methoxyphenylnitromethane, dinitroethane, dinitrohexane, dinitrocyclohexane, di-(nitrohexyl)methane, etc. Further, the isomers, mixtures or homologues of these compounds may also be used. The amines and nitro compounds used in the present invention are preferred to have the same skeletal structure, although they may have different ones.

The process of the present invention may be carried out in the absence of solvents, but solvents may be used.

As such solvents, at least one solvent selected from the following ones or mixtures thereof may be used:

aromatic hydrocarbons such as benzene, toluene, xylene, etc., nitriles such as acetonitrile, propionitrile, benzonitrile, etc., organophosphoric compounds such as HMPA (hexamethylphosphoramide), sulfolanes such as sulfolane, dimethylsulfolane, etc., halogenated, aromatic hydrocarbons such as monochlorobenzene, dichlorobenzene, etc., heptane, methylcyclohexane, ketones, esters, THF, 1,4-dioxane, propylene carbonate, N-methylpyrrolidone, 1,2-dimethoxyethane, etc.

CO used in the present invention may be used alone or in admixture of another gas, preferably $H_2$ gas. As these gases, petroleum fractions like naphtha, etc., gas obtained from coal gasification, by-produced gases at various ironworks may be utilized.

In the process of the present invention, water should be existed in advance of the reaction, molar ratio of the water in terms of 1 mol of the amino group-containing compound being in the range of 0.01 to 2.0 (mol). This water may be that of the aqueous solution of a hydrogen halide to be added in the reaction. However, an excess concentration of water in the aqueous solution of a hydrogen halide is undesirable since the reaction rate is reduced. The concentration of the aqueous solution of a hydrogen halide is preferably in the range of 500 to 5000 ppm.

As to the ratio of the hydroxyl group-containing organic compound to the amino group-containing compound fed, used in the present invention, the molar ratio of hydroxyl group is 3 to 40 times, preferably 8 to 35 times the molar ratio of amino group. The hydroxyl group-containing organic compound may also be used as the above-mentioned solvent.

As to the quantity of the nitro group-containing organic compound used, the molar ratio of nitro group is 0.1 to 2.0 times, preferably 0.4 to 1.2 times the molar ratio of amino group. A part of the nitro group-containing organic compound may be replaced by oxygen. When $O_2$ is used at the same time, it is possible to reduce the quantity of the nitro group-containing compound used.

The reaction pressure is 1 to 50 $Kg/cm^2G$, preferably 5 to 30 $Kg/cm^2G$ in terms of the partial pressure of CO. The reaction temperature is preferably 60° to 230° C., more preferably 150° to 190° C.

The reaction time varies depending on the kind of the nitrogen compounds and other reaction conditions, but the reaction is carried out generally in the range of 5 minutes to 6 hours. After completion of the reaction, the reaction mixture is cooled, followed by evacuating, separating the catalyst from the reaction mother liquor by filtration or the like means, and separating the aimed carbamic acid ester free of unreacted substances, solvent, etc. from the mother liquor by distillation or other suitable separating means.

After completion of the reaction, if desired, hydrogen gas is introduced into the resulting reaction solution to convert unreacted nitro group (i.e. nitrobenzene) into amino group (i.e. aniline), followed by separating the resulting carbamic acid ester from the reaction mixture by distillation or another suitable separating means.

Next, the present invention will be illustrated by way of flowsheets.

FIG. 1 shows a flowsheet illustrating an embodiment of production of the carbamic acid ester in the present invention. In this figure, a CO-containing gas A is pressurized and fed into synthetic column 1. Further, aniline J, nitrobenzene B, ethanol C and recovered ethanol F are fed into synthetic column 1. Platinum group catalyst/carrier 11 has been filled in the synthetic column 1 and reaction is effected at a definite reaction temperature, a reaction pressure and a reaction time. The reaction solution may also be circulated through the inside of synthetic column 1 by means of a pump to sufficiently effect its contact with the catalyst. Unreacted CO gas is freed from by-produced gas $CO_2$(E) and then circulated into synthetic column 1. Here, water, ethanol, solvent, etc. can be withdrawn from the top of the column, while aniline, nitrobenzene and ethyl N-phenylcarbamate (NPU) can be withdrawn from the bottom of the column. The solution withdrawn from the bottom of the column is led to conversion column 21. A hydrogen-containing gas D is pressurized and fed into conversion column 21. The resulting reaction solution is led to low boiling distillation column 2. The low boiling distillation in the column 2 is operated at 100° to 120° C. The solution withdrawn from the bottom of low boiling column 2 is led to distillation column 4 where distillation is carried out at a temperature of 180° to 200° C., and ethyl N-phenylcarbamate I is recovered from the bottom of the column. The solution from the top of low boiling distillation column 2 is freed from by-produced water G in dehydration column 3 and circulated to synthetic column 1 as a feed F (recovered ethanol). Solution H recovered from the top of distillation column 4 is also circulated to synthetic column 1 as a feed H. Ethyl N-phenylcarbamate (NPU) I is recovered from the bottom of distillation column 4.

Figure 2:
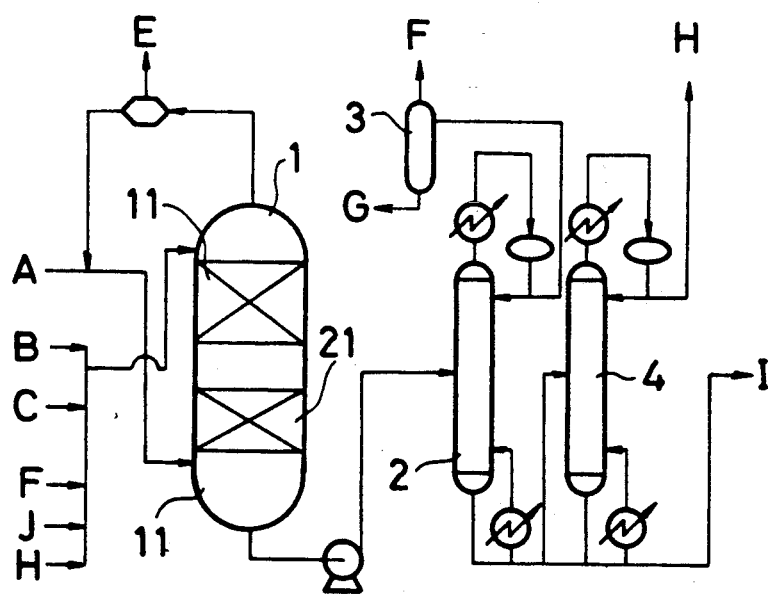
FIG. 2 shows a flowsheet illustrating another embodiment of production of the carbamic acid ester in the present invention.

FIG. 2 shows a flowsheet illustrating another embodiment of production of the carbamic acid ester of the present invention. Gas A containing hydrogen and CO is pressurized and fed into the lower part of a column composed of synthetic column 1 and conversion column 21. Further, aniline J, nitrobenzene B and ethanol C as raw materials and recovered ethanol F and recovered solution H are fed to the upper part of the above-mentioned column. Platinum catalyst/carrier 11 has been filled in synthetic column 1 and conversion column 21, and reaction is operated at a definite reaction temperature, a reaction pressure and a reaction time. The solution withdrawn from the bottom of conversion column 21 is distilled in the same manners as in FIG. 1 and carbamic acid ester I is recovered.

The present invention will be described in more detail by way of Concrete Examples, but it should not be construed to be limited thereto.

EXAMPLE 1

Alumina (1 g) was impregnated with an aqueous solution of Pd(NO$_3$)$_2$, followed by drying at 110° C. for 2 hours and further drying at 500° C. for 2 hours to prepare a catalyst supported by the carrier. The catalyst was PdO and had 3.44% by weight in terms of Pd.

Into a 100 ml capacity SUS 316 stainless autoclave were fed the above catalyst (61.9 mg) (0.020 mmol in terms of Pd), aniline (0.931 g, 0.010 mol), nitrobenzene (1.23 g, 0.010 mol), ethanol (4.61 g, 0.10 mol), toluene (10.6 g, 0.11 mol) and 35% hydrochloric acid aqueous solution (0.071 g, HCl=0.68 mmol, H$_2$O=0.067 mmol), followed by introducing CO gas up to 28 Kg/cm$^2$ at room temperature without purging the air inside the system, reacting them at a reaction temperature of 190° C. for 3 hours, cooling the reaction mixture down to room temperature after the reaction, returning the pressure inside the system to the atmospheric pressure and analyzing the reaction product according to gas chromatography. As a result, ethyl N-phenylcarbamate (NPU) (2.97 g) was formed (NPU yield: 90%), and aniline (0.093 g, 0.001 mol) and nitrobenzene (0.123 g, 0.001 mol) remained unreacted.

The reaction solution was distilled at a temperature of 200° C. and under a reduced pressure of 10 Torr. As a result of analyzing the residual solution after the distillation, the NPU purity was 95%, the contents of nitrobenzene and aniline were 5% and 0.1%, respectively and no decomposition product of NPU was found.

In the case where the reaction solution was distilled at a temperature of 230° C. and under the atmospheric pressure, followed by analyzing the residual solution, the NPU purity was 60%, the contents of nitrobenzene and aniline were 19% and 0.1%, respectively and a decomposition product of NPU was observed in a portion.

EXAMPLE 2

Example 1 was repeated except that gases of hydrogen partial pressure 1 atm and CO partial pressure 28 atm were used. The reaction product was analyzed according to gas chromatography and liquid chromatography. As a result, NPU (2.97 g) was formed and aniline (0.124 g, 0.0013 mol) and nitrobenzene (0.082 g, 0.007 mol) remained unreacted.

The solution after completion of the reaction was distilled at a temperature of 200° C. and under a reduced pressure of 10 Torr. As a result of analyzing the residual solution after the distillation, the NPU purity was 96%, the contents of nitrobenzene and aniline were 4% and 0.1%, respectively and no decomposition product of NPU was found.

EXAMPLE 3

Hydrogen gas is introduced into the reaction solution obtained in Example 1 to convert unreacted nitrobenzene contained in the solution into aniline, followed by cooling the resulting solution down to room temperature, returning the pressure inside the system to the atmospheric pressure and analyzing the reaction product according to gas chromatography and liquid chromatography. As a result, ethyl N-phenylcarbamate (NPU) (2.97 g) was formed (NPU yield: 90%), and the quantities of aniline and nitrobenzene were 0.186 g (0.002 mol) and 0.0001 g or less, respectively.

The above solution was distilled at a distillation operation temperature of 230° C. and under the atmospheric pressure, followed by analyzing the residual solution. As a result, the NPU purity was 99%, the contents of nitrobenzene and aniline were 0% and 0.1%, respectively.

EXAMPLES 4-6

Example 1 was repeated except that the quantities of ethanol and toluene were varied as shown in Table 1. The results are shown in Table 1.

TABLE 1

| Example | 4 | 5 | 6 |
| --- | --- | --- | --- |
| Ethanol, g | 2.77 | 3.69 | 5.53 |
| (mol) | (0.06) | (0.08) | (0.12) |
| Toluene, g | 12.7 | 11.6 | 9.62 |
| NPU, g | 2.03 | 2.38 | 2.49 |
| Yield (%) | 89.9 | 72.0 | 75.4 |

EXAMPLES 7-9 AND COMPARATIVE EXAMPLE 1 AND 2

Example 1 was repeated except that the quantities of aniline and nitrobenzene were varied as shown in Table 2. The results are shown in Table 2.

TABLE 2

|  | Ex. 7 | Ex. 8 | Comp. ex. 1 | Comp. ex. 2 |
| --- | --- | --- | --- | --- |
| Aniline, g | 0.931 | 0.931 | 1.86 | 0 |
| (mol) | (0.01) | (0.01) | (0.02) |  |
| Nitrobenzene, g | 0.985 | 1.35 | 0 | 2.46 |
| (mol) | (0.005) | (0.011) |  | (0.02) |
| NPU, g | 2.57 | 2.61 | 0.0901 | 0.482 |
| Yield (%) | 77.8 | 79.0 | 27.3 | 14.6 |

EXAMPLES 9-11

Example 1 was repeated except that the concentration of HCl fed was varied as shown in Table 3. When the HCl quantity exceeded 0.68 mmol, aniline hydrochloride was added for adjustment. The water quantity was made definite to 0.067 mmol. The results are shown in Table 3.

TABLE 3

| Example | 9 | 10 | 11 |
| --- | --- | --- | --- |
| HCl (mmol) | 0.50 | 1.36 | 2.40 |
| NPU (g) | 2.39 | 2.94 | 2.61 |
| Yield | 72.3 | 89.0 | 79.0 |

EXAMPLE 12

Example 1 was repeated except that the water quantity was made 14 mmols to obtain NPU (2.72 g, yield: 82.3%).

EXAMPLE 13

Aniline (0.780 g), aniline hydrochloride (0.0881 g), nitrobenzene (1.35 g), ethanol (4.61 g), toluene (10.6 g), 35% hydrochloric acid aqueous solution (0.071 g) and the catalyst supported by a carrier, which was used in Example 1, (61.9 mg) were fed into the same autoclave used in Example 1, followed by introducing $H_2$ gas under 1 atm and CO gas under 28 Kg/cm$^2$·G, reacting them at 190° C. for 6 hours and analyzing the resulting product as in Example 1, to form NPU (3.05 g, Yield: 92.3%).

EXAMPLE 14

Example 1 was repeated except that ethanol (14.4 g) was used as a reactant and at the same time as a solvent without using toluene and aniline (0.771 g) and aniline hydrochloride (0.2229 g) were used, to obtain NPU (2.95 g, Yield: 89.3%).

COMPARATIVE EXAMPLE 3

Example 1 was repeated except that as HCl, 35% hydrochloric acid was replaced by aniline hydrochloride. As a result, only 1.97 g of NPU was formed (Yield: 59.6%). As seen from the above experiment, it is important that a small quantity of $H_2O$ is introduced in advance.

EXAMPLE 15

Example 1 was repeated except that the inside of the reaction vessel was purged with $N_2$. As a result, only 2.32 g of NPU was formed (Yield: 70.2%).

According to the present invention, when carbamic acid esters are produced from an amino group-containing compound, a nitro group-containing compound, a CO-containing gas and a hydroxyl group-containing organic compound in the presence of a Pt group metal compound, it is possible to increase the formation rate of NPU as compared with that of conventional process, by making water coexistent, and since the catalyst used in the present invention does not require to slurry the solution, the processing capacity of the raw materials is large. Further, recovery of the catalyst and separation of carbamic acid esters are easily performed, especially by further adding hydrogen to the reaction mixture. Thus, the process of the present invention is a commercially advantageous process.

What we claimed is:

1. A process for producing carbamic acid esters which comprises reacting an amino group-containing compound, oxygen and a nitro group-containing organic compound, a carbon monoxide-containing gas and a hydroxyl group-containing organic compound in the presence of a compound of a transition metal belonging to Pt group of VIII group of the Periodic Table as catalyst, a non-metal halide and water, the molar ratio of said nitro group-containing organic compound to be reacted being 0.1 to 2.0 times the molar ratio of the amino group of the amino group-containing compound, the molar ratio of said hydroxyl group-containing organic compound to be reacted being 3 to 40 times the molar ratio of the amino group of the amino group-containing compound, the pressure of said carbon monoxide-containing gas being in the range of 1 to 50 $Kg/cm^2G$, and molar ratio of said water to be existed in advance of the reaction in terms of the amino group-containing compound being in the range of 0.01 to 2.0.

2. A process for producing carbamic acid esters according to claim 1, wherein said transition metal is at least one selected from Pt, Pd, Rh and Ru.

3. A process for producing carbamic acid esters according to claim 1, wherein said non-metal halide is a hydrogen halide or an ammonium halide.

4. A process for producing carbamic acid esters according to claim 1, said non-metal halide is hydrogen chloride.

5. A process for producing carbamic acid esters according to claim 1, wherein said amino group-containing compound is at least one selected from aromatic or aliphatic monoamines, aromatic or aliphatic polyamines, and aromatic or aliphatic amino acids.

6. A process for producing carbamic acid esters according to claim 1, wherein said amino group-containing compound is aniline.

7. A process for producing carbamic acid esters according to claim 1, wherein said nitro group-containing organic compound is at least one selected from aromatic or aliphatic mononitro compounds and aromatic or aliphatic polynitro compounds.

8. A process for producing carbamic acid esters according to claim 1, wherein said nitro group-containing organic compound is nitrobenzene.

9. A process for producing carbamic acid esters according to claim 1, wherein said hydroxyl group-containing organic compound is at least one selected from monohydric or polyhydric alcohols and monohydric or polyhydric phenols.

10. A process for producing carbamic acid esters according to claim 1, wherein said hydroxyl group-containing organic compound is methanol or ethanol.

11. A process for producing carbamic acid esters according to claim 1, wherein the resulting reaction mixture is contacted with hydrogen to convert unreacted nitro group-containing organic compound into amino group-containing compound, followed by separating the resulting carbamic acid ester from the reaction mixture by distillation.

12. A process for producing carbamic acid esters according to claim 1, wherein said carbon monoxide containing gas contains hydrogen.

13. A process for producing carbamic acid esters according to claim 1 wherein the only metal halide present in said reaction is a compound of a transition metal belonging to the platinum group of VIII periodic table.

* * * * *